(12) United States Patent
Bloebaum et al.

(10) Patent No.: US 10,864,082 B2
(45) Date of Patent: Dec. 15, 2020

(54) OSTEOLYSIS-RESISTANT CEMENTLESS JOINT IMPLANT WITH IMPROVED STABILITY AND SEATING FUNCTION

(71) Applicants: Roy D. Bloebaum, Salt Lake City, UT (US); Efrain Frank Algarin, Salt Lake City, UT (US)

(72) Inventors: Roy D. Bloebaum, Salt Lake City, UT (US); Efrain Frank Algarin, Salt Lake City, UT (US)

( * ) Notice: Subject to any disclaimer, the term of this patent is extended or adjusted under 35 U.S.C. 154(b) by 153 days.

(21) Appl. No.: 16/165,387

(22) Filed: Oct. 19, 2018

(65) Prior Publication Data
US 2020/0121465 A1 Apr. 23, 2020

(51) Int. Cl.
*A61F 2/38* (2006.01)
*A61F 2/30* (2006.01)

(52) U.S. Cl.
CPC ...... *A61F 2/30749* (2013.01); *A61F 2/30771* (2013.01); *A61F 2/389* (2013.01); *A61F 2/3859* (2013.01); *A61F 2002/3021* (2013.01); *A61F 2002/3041* (2013.01); *A61F 2002/30179* (2013.01); *A61F 2002/30205* (2013.01); *A61F 2002/30224* (2013.01); *A61F 2002/30433* (2013.01); *A61F 2002/30841* (2013.01)

(58) Field of Classification Search
CPC .. A61F 2/30749; A61F 2/30771; A61F 2/389; A61F 2/3859; A61F 2002/30433; A61F 2002/30205; A61F 2002/30224; A61F 2002/30179; A61F 2002/30841; A61F 2002/3021; A61F 2002/3041
See application file for complete search history.

(56) References Cited

U.S. PATENT DOCUMENTS

| 4,257,129 A * | 3/1981 | Volz | A61F 2/389 623/20.33 |
| 6,379,388 B1 * | 4/2002 | Ensign | A61F 2/4637 623/20.34 |
| 6,652,588 B2 * | 11/2003 | Hayes, Jr. | A61L 27/306 623/20.32 |
| 6,746,486 B1 * | 6/2004 | Shultz | A61F 2/4261 623/21.12 |
| 6,905,513 B1 * | 6/2005 | Metzger | A61F 2/08 623/20.14 |
| 7,326,252 B2 * | 2/2008 | Otto | A61F 2/3886 623/20.15 |
| 7,422,605 B2 * | 9/2008 | Burstein | A61F 2/3868 623/20.32 |
| 7,766,969 B2 * | 8/2010 | Justin | A61F 2/389 623/20.15 |
| 7,981,159 B2 * | 7/2011 | Williams | A61F 2/3868 623/20.21 |

(Continued)

*Primary Examiner* — Amy R Weisberg
(74) *Attorney, Agent, or Firm* — Steven Rinehart

(57) ABSTRACT

An improvised anthroplastic prosthetic implant having, in some embodiments, secondary screws with threaded shafts for forming pilot holes into the resected cancellous bone surface, such as the tibia, and primary screws with tapered heads for replacing the secondary screws and forming a Morse friction fit with the implant and seating the implant in close apposition to, and at less than 150 um in, resected bone thereby facilitating implant stability, wherein the heads of the primary screws are recessed into a counterbore in the baseplate to improve axial postoperative stability of the implant.

14 Claims, 6 Drawing Sheets

(56) References Cited

U.S. PATENT DOCUMENTS

| | | | | |
|---|---|---|---|---|
| 7,998,203 B2* | 8/2011 | Blum | A61B 17/1714 | 623/13.12 |
| 8,500,817 B2* | 8/2013 | Farrar | A61F 2/3859 | 623/20.27 |
| 8,540,776 B2* | 9/2013 | Bercovy | A61F 2/3868 | 623/20.21 |
| 8,696,755 B2* | 4/2014 | Mandell | A61F 2/30734 | 623/20.32 |
| 9,060,866 B2* | 6/2015 | Fankhauser | A61F 2/38 | |
| 2003/0083658 A1* | 5/2003 | Hawkes | A61F 2/34 | 606/279 |
| 2003/0216813 A1* | 11/2003 | Ball | A61F 2/4261 | 623/21.12 |
| 2005/0010302 A1* | 1/2005 | Dietz | A61B 5/4528 | 623/20.21 |
| 2005/0033298 A1* | 2/2005 | Hawkes | A61F 2/34 | 606/281 |
| 2005/0203631 A1 | 9/2005 | Daniels | | |
| 2005/0203632 A1* | 9/2005 | Daniels | A61F 2/389 | 623/20.34 |
| 2005/0261775 A1* | 11/2005 | Baum | A61F 2/4081 | 623/19.12 |
| 2006/0224244 A1* | 10/2006 | Thomas | A61L 27/26 | 623/20.28 |
| 2007/0135924 A1* | 6/2007 | Verhoogen | A61B 17/1675 | 623/18.11 |
| 2007/0288021 A1* | 12/2007 | Rickels | A61B 17/1764 | 606/916 |
| 2008/0021565 A1* | 1/2008 | Hayes, Jr. | A61L 27/045 | 623/20.14 |
| 2008/0114462 A1* | 5/2008 | Guidera | A61F 2/3868 | 623/20.27 |
| 2008/0215156 A1* | 9/2008 | Duggal | A61F 2/42 | 623/18.11 |
| 2008/0300690 A1* | 12/2008 | Burstein | A61F 2/3868 | 623/20.29 |
| 2009/0265013 A1* | 10/2009 | Mandell | A61F 2/38 | 623/20.21 |
| 2009/0306784 A1* | 12/2009 | Blum | A61F 2/38 | 623/20.21 |
| 2014/0277544 A1* | 9/2014 | Viscogliosi | A61B 17/3472 | 623/20.32 |
| 2014/0296990 A1* | 10/2014 | Shaw | A61F 2/38 | 623/20.21 |
| 2016/0192878 A1* | 7/2016 | Hunter | A61B 5/0031 | 623/20.14 |
| 2017/0042683 A1* | 2/2017 | Hansen | A61F 2/30 | |
| 2018/0153598 A1* | 6/2018 | Jurick | A61F 2/389 | |
| 2018/0271668 A1* | 9/2018 | Kemp | A61F 2/4014 | |
| 2019/0105177 A1* | 4/2019 | Piecuch | A61F 2/30749 | |

* cited by examiner

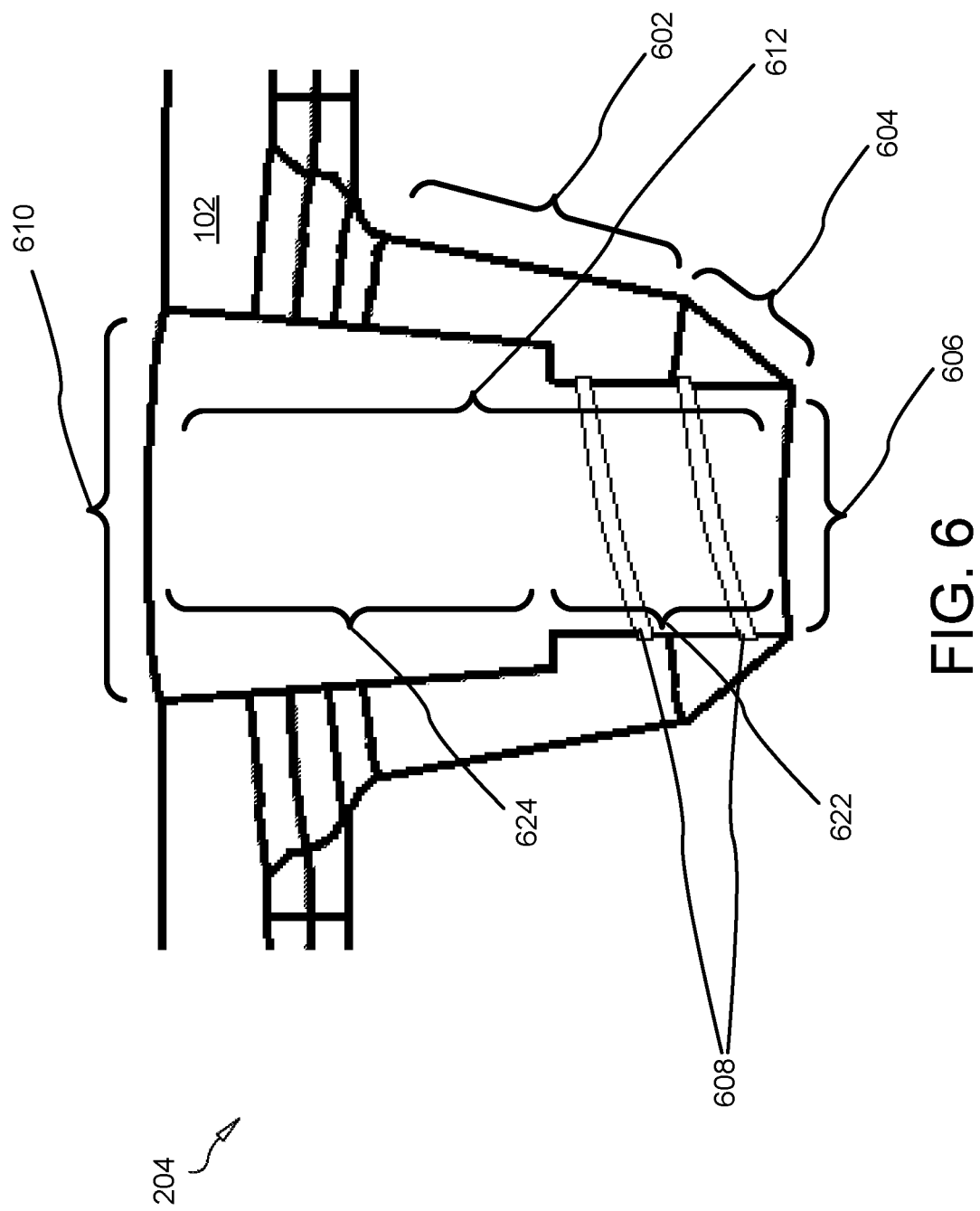

OSTEOLYSIS-RESISTANT CEMENTLESS JOINT IMPLANT WITH IMPROVED STABILITY AND SEATING FUNCTION

FIELD OF THE INVENTION

This invention relates to prosthetic devices, and more particularly relates to implants and artificial joints used in arthroplasty.

BACKGROUND

Description of the Related Art

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Total joint arthroplasty is the surgical replacement of a joint with a prosthesis or endoprostheses. A typical knee prosthesis used in joint arthroplasty comprises a femoral implant, a tibial implant, and a patellar implant, and a tibio-femoral (or bearing) insert. The femoral and tibial implants are adapted to replace the articular surfaces which may become damaged as a result of accident, disease or wear. The articular cartilage covering the ends of the bones at the joint as well as the intra-articular cartilage between the ends of the adjacent bones of the joint wear as a patient ages often necessitating implantation of a joint replacement to improve the comfort and mobility of the patient.

Joint replacements have been developed to replace native tissue of several human joints and typically consist of the bone interface of the distal end of the femur and the proximal end of the tibia as well as the patella.

When a joint such as a knee or hip becomes damaged, osteophyte projections and articular cartilage erosion occurs leading to joint pain. Joint replacements may be used to restore pain free articulation.

These implants are typically anchored in the intramedullary canal and cancellous bone of the femur, tibia, or other bones, and consist of keels or anchors extending downwardly therefrom into cancellous bone located at the end of long bones to provide a compliant mechanical environment to assure skeletal attachment. Cancellous bone may also be referred to as trabecular bone because of the porous nature of the bone (from 80-88%) and/or spongiosa bone because of the compliant mechanical properties to protect the articular cartilage from mechanical damage and arthritis during loading of the joint.

When considering the attachment of a cementless/porous coated joint replacement to the spongiosa bone, one also needs to understand the loading capacity and the mechanical requirements for bone ingrowth and ongrowth to assure secure implant attachment to prevent mechanical loosening.

It has been established there are major factors that must be addressed to assure long term mechanical stability and attachment in joint replacements. One is the limiting motion (rotational and axil) below 150 um between the cementless or porous coated surface and another is to assure the cementless or porous coated surface is placed within the 50-150 um of the resected or surgically prepared surface to allow the cancellous bone attachment during the three months it takes for human bone to attach to the cementless or porous coated material.

The best way to assure the mechanical attachment during the axial and rotational loads that occur in a joint replacement is the use of pegs and screws to mechanically secure the joint replacement device such as the tibial component in total knee replacements. It has been shown clinically that the problem with screws is that it is common that the screw head is not completely seated within the implants allowing wear particulates to track along the screw surface leading to bone loss due to osteolysis and the mechanical failure of the implant requiring removal. This bone loss can be severe leading to early removal while compromising the following revision surgery due to the severe bone loss.

Although some implant designs combine screws and anti-rotational elements, none allow for the screw head to be sealed and captured in the canal of a peg which also serves to prevent rotational loads. Having the peg with canal alone then implanting the device into the bone can lead to the clogging of the canal and make the screw head defect, leaving an opening for wear and screw track osteolysis. Another problem with pegs is if they are not completely seated under surface of the implant stress shielding occurs preventing bone attachment.

There are no implants in the art which cure these deficiencies. With the foregoing in mind, therefore, a primary objective of the present invention is to provide cementless joint implants having means adapted to securely seat and affix the implant in long bone while preventing screw track osteolysis.

A more specific object of this invention is to provide an implant which is some embodiments comprises primary and secondary screws used successively in concert with one another, and using a Morse cold weld, to securely seat the implant in long bone and seal the screw track from osteolysis. In view of the foregoing, it should be clear that there is a need in the industry for an apparatus and means of more efficiently seating and sealing the screw track from particulate wear in cementless joint replacements.

SUMMARY

From the foregoing discussion, it should be apparent that a need exists for an osteolysis-resistant cementless joint implant with improved stability and seating function. Beneficially, such an apparatus would provide means of securely seat said implant and sealing the screw track, along a plurality of features and components efficacious for helping to cure the above-described deficiencies in the prior art.

The present invention has been developed in response to the present state of the art, and in particular, in response to the problems and needs in the art that have not yet been fully solved by currently available apparatus. Accordingly, the present invention has been developed to provide a prosthetic implant for apposition on a resected surface of a bone, the implant comprising: a baseplate having a substantially planar lower apposition surface and an upwardly rising perimeter edge which forms a tray-like depression surface for receiving a tibio-femoral insert; one or more elongate conical anchors protruding inferiorly from the apposition surface, each conical anchor defining a hollow interior throughpassage for receiving, mating with, and forming a Morse friction fit with, a tapered screw head received via the through-cavity; two or more primary socket head shoulder screws comprising a tapered head and threaded shaft; and two or more secondary socket head screws comprising a tapered head, a sharpened conical tip, and a threaded cylindrical shaft; wherein the secondary socket head screws are placed into the implant prior to surgical impaction of the implant to form pilot holes and replaced with the primary socket head shoulder screws after surgical impaction of the implant, the primary socket head shoulder screws forming a Morse taper with the through-cavity adapted to create a seal within the through cavity to prevent osteolysis.

The prosthetic implant may further comprise an elongate, tapered keel member protruding inferiorly from the apposition surface. The prosthetic implant may further comprise one or more sharpened pegs protruding inferiorly from the apposition surface.

The hollow interior through-passage may consist of an upper section tapered to form a Morse taper with one or more of a primary socket head shoulder screw and a secondary socket head screw.

The hollow interior through-passage may consist of a lower section threaded to mate with a secondary socket head shoulder screw to prevent the displacement of the secondary screw during implant impaction.

Each conical anchor may comprise a frustoconical tip. Each peg may comprise a frustoconical tip. The keel may be X-shaped through a cross-section.

A second prosthetic implant for apposition to the resected surface of a bone is provided, the implant comprising: a baseplate having a substantially planar lower apposition surface; an elongate, tapered keel member protruding inferiorly from the apposition surface; one or more sharpened pegs protruding inferiorly from the apposition surface; one or more elongate protuberating anchors protruding inferiorly from the apposition surface, each protuberating anchor defining a hollow interior through-passage for receiving, mating with, and forming a Morse friction fit with, a tapered screw head received by the through-cavity; two or more primary screws, each comprising a tapered head and threaded shaft; and two or more secondary screws, each comprising a tapered head, a threaded cylindrical shaft and sharpened conical tip; wherein the secondary screws are placed into the implant prior to surgical impaction of the implant and replaced with the primary screws after surgical impaction of the implant, the primary screws penetrating deep into the cancellous bone forming a Morse taper with the protuberating anchor adapted to impart axial mechanical stability to the primary screws.

The hollow interior through-passage may consist of an upper section tapered to form a Morse taper with one or more of a primary screw and a secondary screw.

The hollow interior through-passage may consist of a lower section threaded to mate with a secondary screw. Each conical anchor may comprise a frustoconical tip.

Each peg may comprise a frustoconical tip. The keel may be X-shaped through a cross-section.

A third prosthetic implant for apposition on a resected surface of a bone is provided, the implant comprising: a baseplate having a substantially planar lower apposition surface; an elongate, tapered keel member protruding inferiorly from the apposition surface; one or more sharpened pegs protruding inferiorly from the apposition surface; one or more conical anchors protruding inferiorly from the apposition surface, each conical anchor defining a hollow interior through-passage for receiving, mating with, and forming a Morse friction fit with, a tapered screw head received by the through-cavity, the Morse friction fit adapted to prevent contaminates from migrating up the through-cavity; wherein the hollow interior through-passage consists of an upper section tapered to form a Morse taper with a primary screw; wherein the hollow interior through-passage consists of a lower section threaded to mate with a screw; wherein each conical anchor comprises a frustoconical tip.

The present invention provides improved axial stability of the screws and prevents contaminants and particulates from migrating beyond the screw seal into the bone. The present invention provides improved heel-toe loading when patients are swinging, stepping, releasing and applying pressure to joints. The joint implant disclosed in the present invention may be used in any mammalian joint, including shoulder or other joint replacements.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 6 is a sectioned, exploded side perspective view illustrating one embodiment of a conical anchor of a cementless joint implant having primary and secondary screws in accordance with the present invention.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method.

Figure 1:
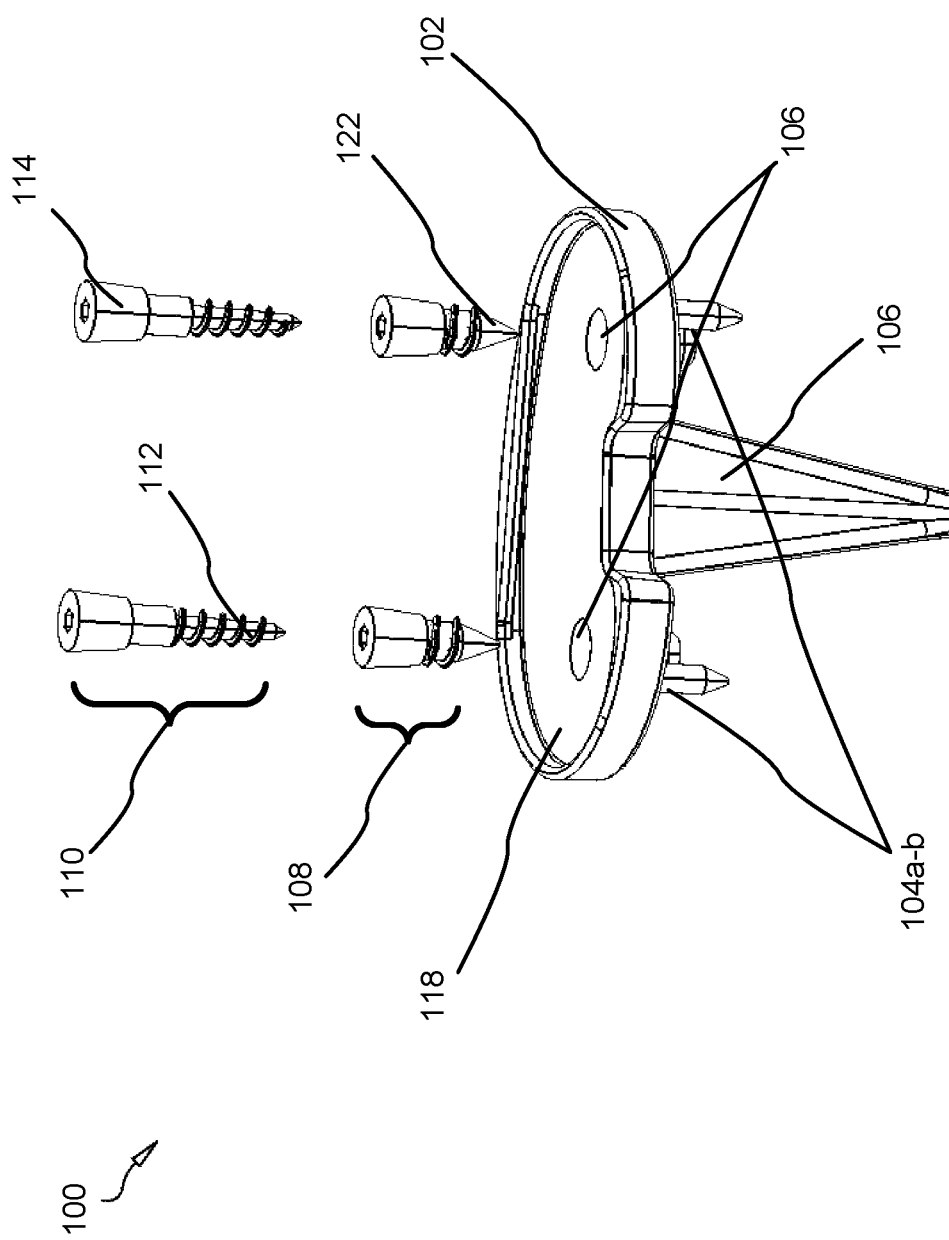
FIG. 1 is a top, side perspective view illustrating one embodiment of cementless joint implant having primary and secondary screws in accordance with the present invention.

FIG. 1 is a top, side perspective view illustrating one embodiment of cementless, joint implant having primary and secondary screws 100 in accordance with the present invention.

The implant 100 may comprise a joint replacement positioned within the tibia, femur, or other resected bone surfaces.

The tray 102 comprises a baseplate formed from a physiologically inert metal adapted to be affixed upon insertion or implantation into a patient using anchor screws, acrylic bone cement or both. The tray 102 comprises a substantially planar lower apposition surface 206 (shown and described below) and an upwardly rising perimeter edge 208 which forms a depression on a concave top surface 118 for receiving a tibio-femoral insert. The tibio-femoral insert may comprise a high-density polyethylene or polymeric member as known to those of skill in the art.

Centrally disposed and downwardly jutting is the principal, elongate, tapered anchoring member, or keel 106, which extends substantially perpendicularly from the lower surface 206 of the tray 102 to a depth within a tibia or adjacent bone in apposition to the lower surface 206 of the tray 102. The elongate, tapered keel member 106 protrudes inferiorly from the apposition surface 206 and inserts into the long bone 502 anchoring the implant 100 and preventing axial rotation thereof within the bone 502.

One or more sharpened pegs 104 or protuberances may protrude inferiorly from the apposition surface 206 into the bone, also serving to prevent axial rotation of the implant 100 when seated. These pegs 104 may be cylindrical, conical, elongate, frustoconical, or any combination of these shapes. The shown implant 100 comprises a plurality of pegs 104, but may comprise only one.

The primary vertical screws 110 are placed into permanent affixation with the bone through conical or cylindrical anchors 204 (described further below) forming a Morse taper between the primary vertical screws 110 and the tray 102 (or baseplate) after the implant 100 is secured with vertical screws 110.

In order to facilitate anchoring/seating (and cementing in some embodiments using acrylic bone cement or other adhesives known to those of skill in the art) of the lower surface 206 within the resected bone, the secondary screws 108 are first inserted into the tray 102 through the bores 106 (or through-passages) as the implant 100 is positioned creating pilot holes for subsequent insertion of the primary vertical screws 110. The secondary screws 108 further assure the advancement of the baseplate 102 into the resected bone. After positioning of the implant 100, the secondary screws 108 are removed and followed by insertion of the primary vertical screws 110 through the bores 106. Clearance between the resected bone surface and the lower surface 206 of the tray 102 is to achieve a less than 150 um gap using this implant 100 thus enabling mechanical stability and bone attachment.

The bores 106 are countersunk into the tray 102 surface such that heads of the screws 108, 110 position at, or inferiorly to, the top surface 118 of the tray 102, mitigating the risk of screw instability and movement which inheres in other designs.

Having distal threading 112 protruding inferiorly to the cylindrical anchor 204 assures the cylindrical anchor 204 is seated surgically within the required 50-150 um distance from the prepared and resected bone and assures peg 104 and/or conical anchors 204 and/or tray 102 seating following the placement of the primary screws 110. Following the impaction process, then the secondary screws 108 held by threads are removed to allow primary screw/permanent screw 110 placement. The screw canal/tunnel 612 of the cylindrical anchor 204 is geometrically-shaped to allow the proximal Morse taper shape of the primary screw 110 head to from a secure seal within the through canal 612 or tunnel assuring mechanical stability between the implant and bone surface.

It is an object of the present invention to facilitate the initial surgical placement of the implant 100 (and its lower surface 206) and to facilitate the seating during impaction by the surgeon. The secondary screws 108 are removed to allow the primary/permanent screws 110 to be placed deeper into the bone to assure axial stability following the removal of the secondary screws 108.

While in place, the secondary screws 108 prevent contaminants/particulates from migrating upward. The primary screws 110, in forming a Morse taper with the conical anchor 204, also prevent contaminants and wear particulates from migrating upward along the screw track (or through-cavity) and wearing the backside of the polyethylene inserts resting in the tray 118. The primary screw 110 facilitates the close apposition of the cementless or porous coated surface and provides mechanically stable for the requisite three-month period. The Morse friction fit and bore 106 (or screw track) within the canal of the cylindrical anchor 204 also serves to prevent mechanical motion between the primary screw 110 and the interior of the cylindrical anchor 204. Therefore, the mechanical objectives of a stable cementless or porous coated implant 100 can achieve rotational and axial stability to assure optimal approximation to the surgically prepared cementless/porous coated surface and resected cancellous bone surface, while preventing screw track osteolysis due to the sealing of the screw 110 proximally within the canal of the cylindrical anchor 204.

Given the objectives of the present invention, screw heads 114 are tapered to form the Morse friction fits within the conical anchors 204. The shafts 112 of the primary screws 110 are threaded to engage bone. Both the primary screws 110 and the secondary screws 108 may comprise shoulder screws. The secondary screws 108 may comprise a conical, sharpened, or tapering tip 122. Both the screws 108, 110 comprise socket head screws in the shown embodiments, but may comprise cap screws or other screws known to those of skill in the art in other embodiments.

Figure 2:
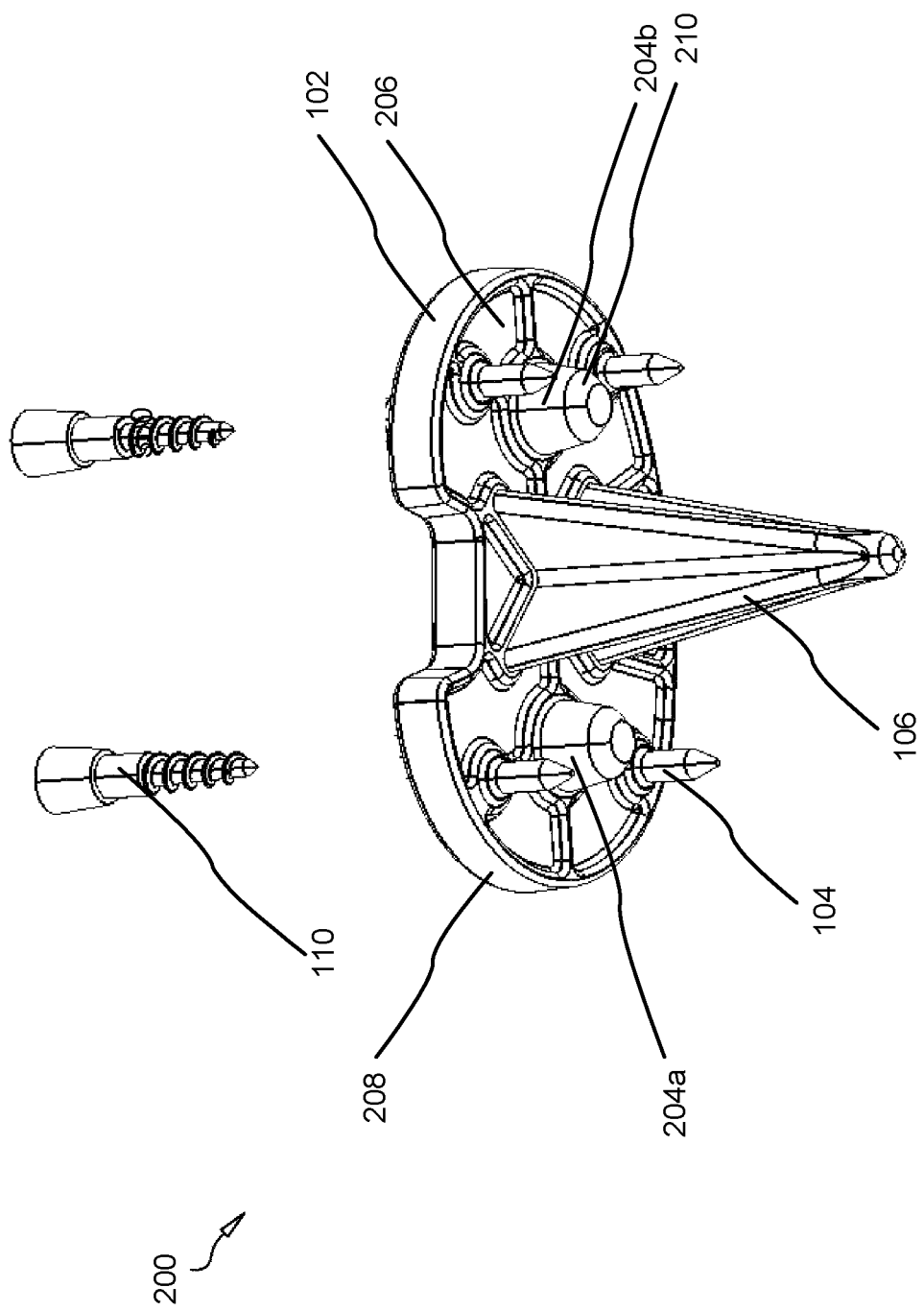
FIG. 2 is a lower, side perspective view illustrating one embodiment of cementless joint implant having primary in accordance with the present invention.

FIG. 2 is a lower, side perspective view illustrating one embodiment of cementless joint implant having primary and secondary screws 200 in accordance with the present invention.

One or more elongate cylindrical anchors 204 protrude inferiorly from the apposition surface 206, each anchor 204 comprising a conical protuberance capped with a frustoconical tip 210 in the shown embodiment.

These cylindrical anchors 204 define a conical through-passage, canal or recess for receiving and forming a Morse cold weld with the heads of screws 108, 110. The screws 108, 110 protrude downwardly through a cylindrical, frustoconical, conical, or boss member downwardly/inferiorly protruding from the lower surface 206 of the tray 102.

Those skilled in the art will recognize that a Morse taper is formed when two substantially identical conically-shaped components mate or engage with one another. This engagement creates a strong surface collision to form a snug, but detachable interconnection or cold weld. An interference, such as a gap between the surfaces further strengthens the surface collision. It is also known in the art that a Morse taper provides a hermetic seal through which wear particulates cannot pass.

A Morse taper coupling may be made between the cylindrical anchors 204 and the screws 108, 110 inserted therein. The screws 108, 110 have or exhibit a truncated-cone head 114 or tang to be forced into a corresponding Morse-tapered female cavity formed inside the cylindrical anchor 204. A Morse taper interaction, or cold weld, between two conical, tapered components, one male on the screws 108, 110 and one female within the cylindrical anchor 204, is activated by axial or impulsive forces exerted using a tool, drift or implement. The angle of the Morse taper mating components may vary with the dimensions of the baseplate 102, but will typically be between 1 and 3.5 degrees. In other words, the taper angle between the head 114 of the primary screw 110 and the taper angle of the upper section 624 of the channel 612 will vary between 1 and 3.5 degrees in the preferred embodiment.

In some embodiments, both the heads 114 of the primary screw 110 and the secondary screws 108 taper to form a Morse taper with the canal 612. In other embodiments, the head 114 of the secondary screws 108 tapers more than is necessary to form a Morse friction fit within the canal 612 such that the secondary screws 108 can be readily extracted and replaced with the primary screws 110.

The keel 106 may be X-shaped through a cross-section as shown.

Figure 3:
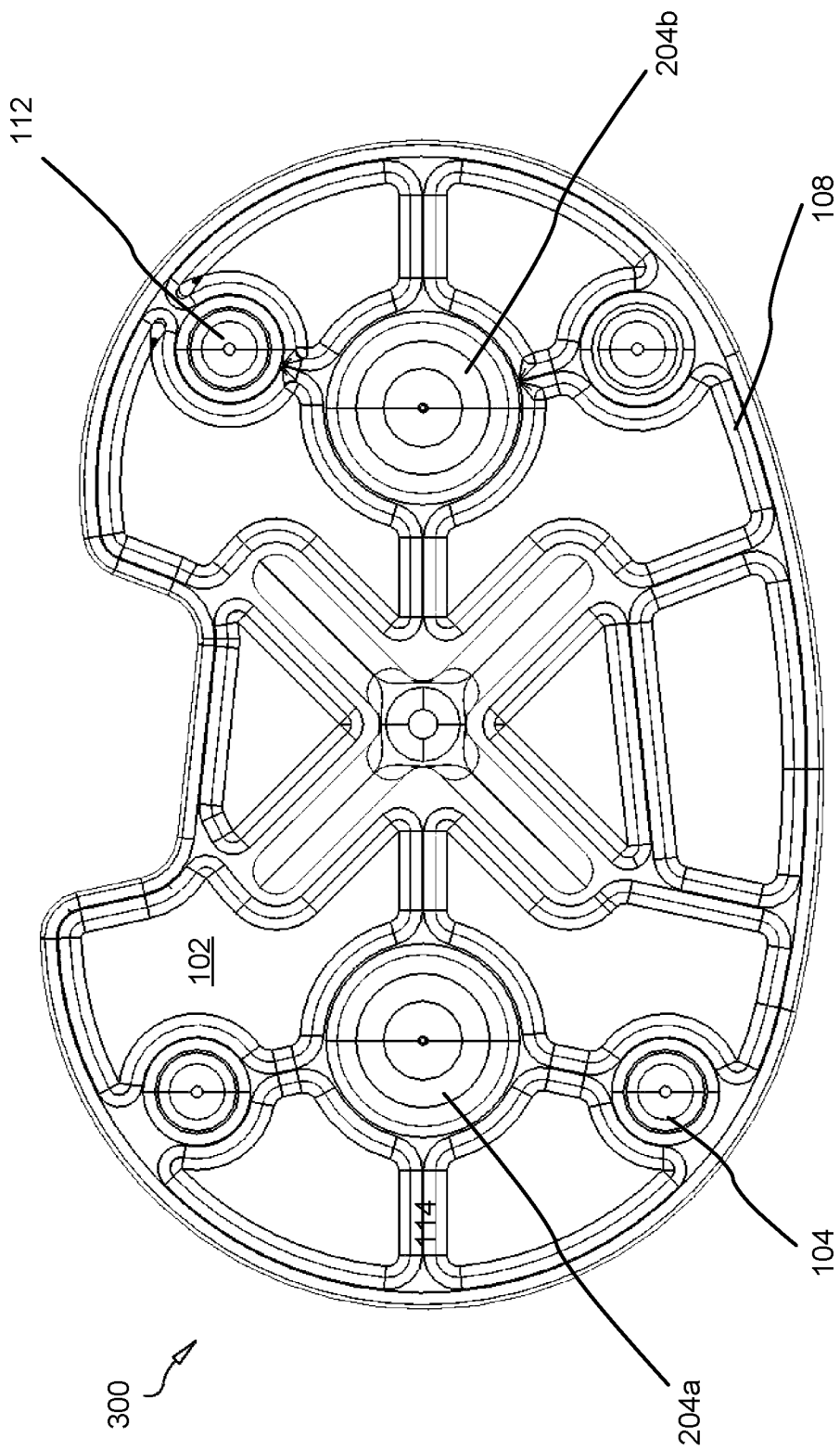
FIG. 3 is a lower perspective view illustrating one embodiment of cementless joint implant having primary and secondary screws in accordance with the present invention.

FIG. 3 is a lower perspective view illustrating one embodiment of cementless joint implant having primary and secondary screws 300 in accordance with the present invention.

As shown.

Figure 4:
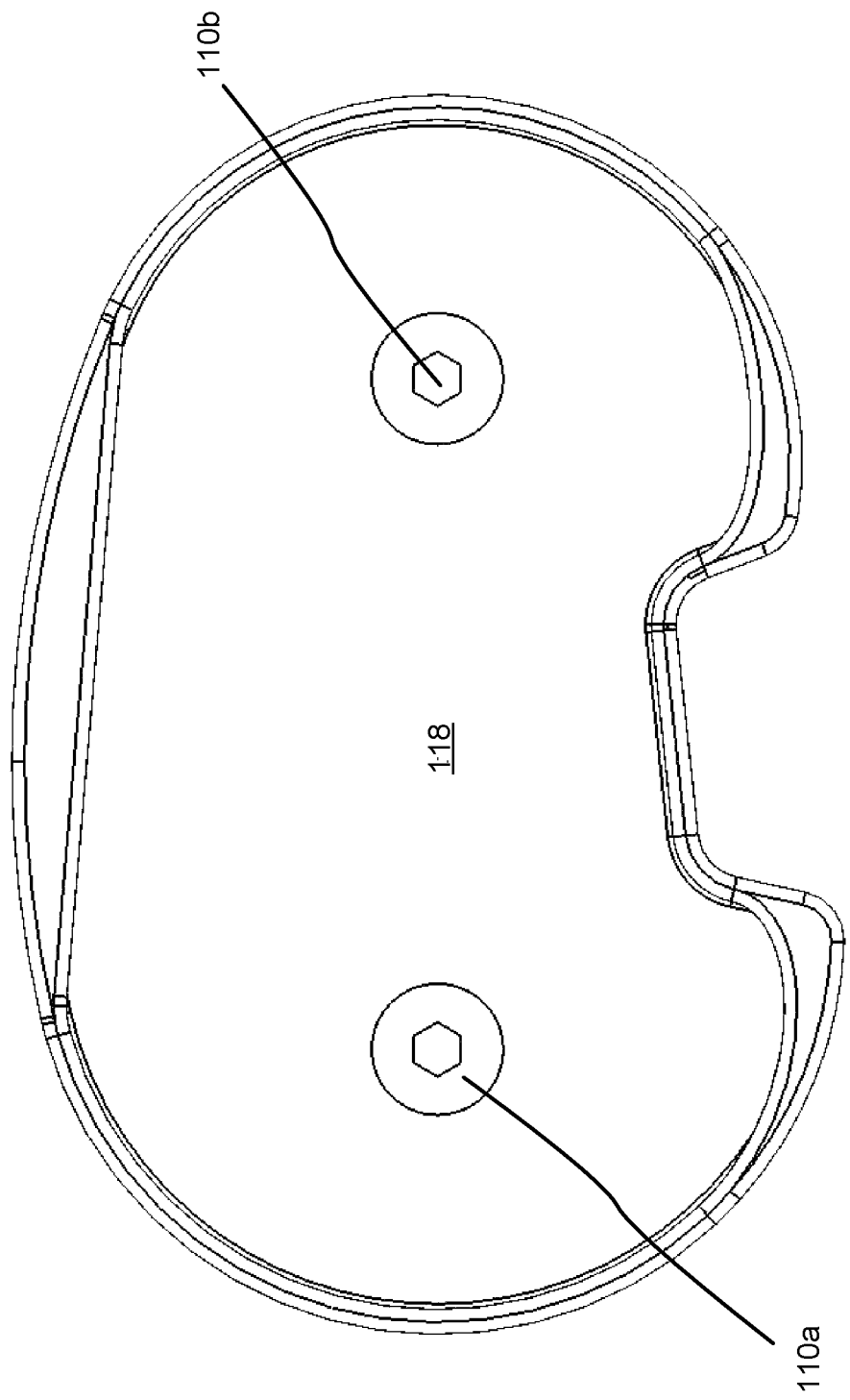
FIG. 4 is a top perspective view illustrating one embodiment of cementless joint implant showing screws seated in the joint implant with the screw heads sealed within the tibial tray in accordance with the present invention.

FIG. 4 is a top perspective view illustrating one embodiment of cementless joint implant having primary and secondary screws in accordance with the present invention.

The screws 110a-b are countersunk into the tray 102 top surface 118.

Figure 5:
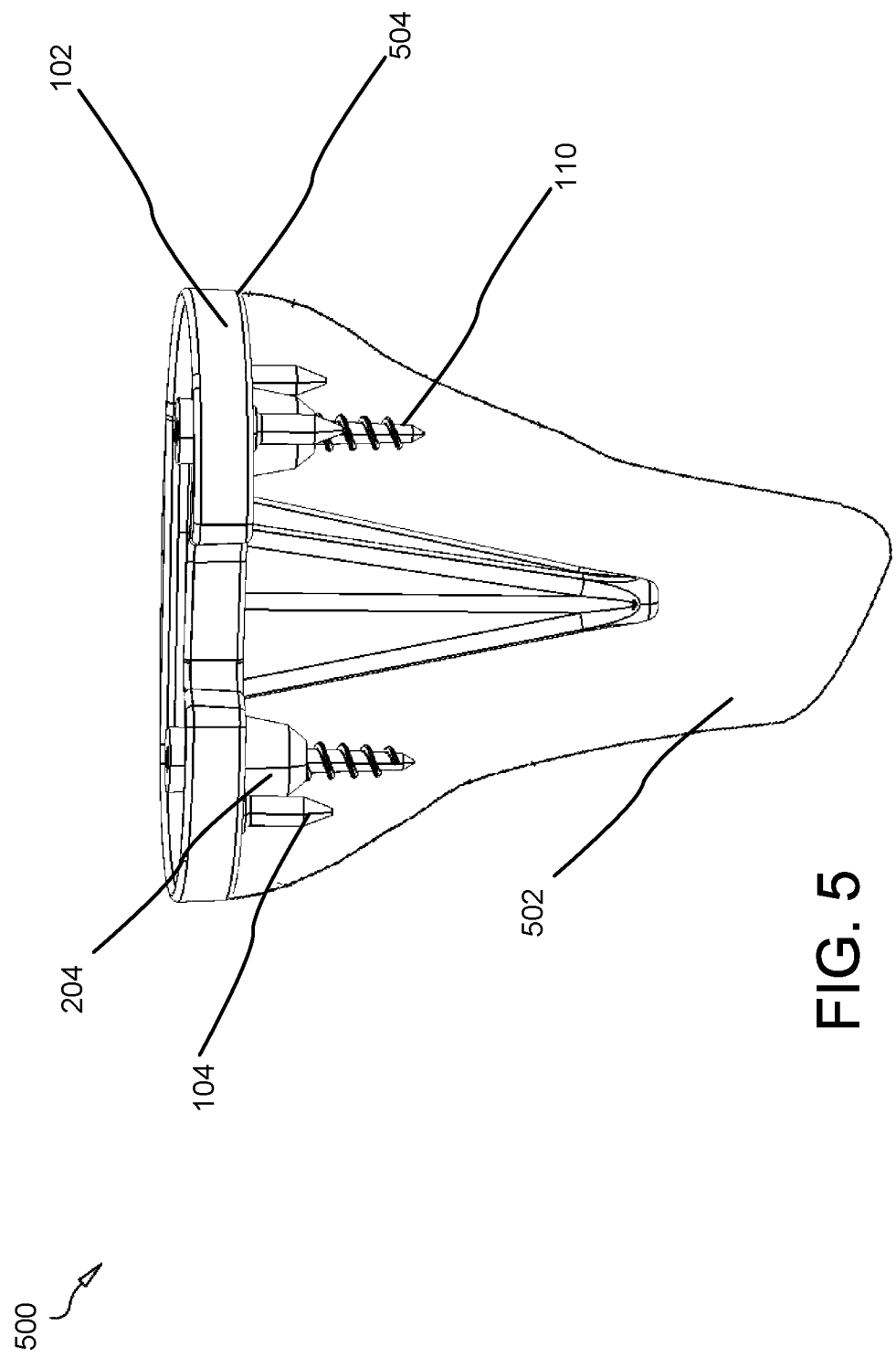
FIG. 5 is an environmental, side perspective view illustrating one embodiment of cementless joint implant having primary and secondary screws in accordance with the present invention.

FIG. 5 is an environmental, side perspective view illustrating one embodiment of cementless joint implant 500 having primary and secondary screws in accordance with the present invention.

The gap 504 between the implant 500 tray 102 and the bone 502 is shown and made to be 50-150 um by the present invention. The implant 500 is seated as shown in the exemplary bone 502.

The secondary screws 108 were previously inserted into the bone 502 and removed preparatory for insertion of the permanent screws 110. In various embodiments, the assembly 500 comprises only the primary screws 110 and not the secondary screws 108. The secondary screws, in some embodiments, may be omitted from the assembly and not used during surgical impaction and placement.

FIG. 6 is a sectioned, exploded side perspective view illustrating one embodiment of a conical anchor 204 of a cementless joint implant having primary and secondary screws in accordance with the present invention.

As shown, a canal, channel or tunnel 612 traverses through the conical anchor 204. The conical anchor 204 defines an open top end 610 and an open bottom end 606 with the canal 612 interconnecting the open top end 610 and the open bottom end 606.

The body 602 of the conical anchor 204 in conically-shaped. A frustoconical tip 604 positioned beneath the body 602 of the conical anchor 204 and may be formed therewith as a single integrated piece, to facilitate impaction and seating.

The interior channel 612 consists of two separate sections 622, 624; an upper section 624 and lower section 622. The upper section 624 is tapered to form a Morse cold friction fit with the head 114 of one or more of the secondary screws 108 and the primary screws 110. The lower section 622 is threaded as shown and cylindrical. The threading 608 is indicated as shown and is sized and dimensioned to receive the threading on the shafts on the secondary screw 108. In this manner, the secondary screws 108 threadably mate with conical anchor 204 and prevent particulates from moving upward as the tray 102 (or baseplate 102) is seated in bone.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An osteolysis-resistant, mechanically stable, prosthetic implant for apposition on a resected surface of a bone, the implant comprising:
   a baseplate having a substantially planar lower apposition surface and an upwardly rising perimeter edge which forms a tray-like depression for receiving a tibiofemoral insert;
   one or more elongate conical anchors protruding inferiorly from the apposition surface, each conical anchor defining a hollow interior through-passage for receiving, mating with, and forming a Morse friction fit with, a tapered screw head received via the through-cavity;
   two or more primary socket head shoulder screws comprising a tapered head and threaded shaft adapted to form a Morse friction fit; and
   two or more secondary socket head screws comprising a sharpened conical tip and a threaded cylindrical shaft;
   wherein the secondary socket head screws are placed into the implant prior to surgical impaction of the implant to form pilot holes and replaced with the primary socket head shoulder screws after surgical impaction of the implant, the primary socket head shoulder screws forming a Morse taper with the through-cavity adapted to seal the through-passage to prevent osteolysis.

2. The prosthetic implant of claim 1, further comprising an elongate, tapered keel member protruding inferiorly from the apposition surface.

3. The prosthetic implant of claim 1, further comprising one or more sharpened pegs protruding inferiorly from the apposition surface.

4. The prosthetic implant of claim 3, wherein each peg comprises a frustoconical tip.

5. The prosthetic implant of claim 1, wherein the hollow interior through-passage consists of an upper section tapered to form a Morse taper with one or more of the primary socket head shoulder screws.

6. The prosthetic implant of claim 1, wherein the hollow interior through-passage consists of a lower section threaded to mate with a secondary socket head shoulder screw.

7. The prosthetic implant of claim 1, wherein each conical anchor comprises a frustoconical tip.

8. The prosthetic implant of claim 1, further comprising a keel.

9. A prosthetic implant for apposition on a resected cancellous surface of a bone, the implant comprising:
   a baseplate having a substantially planar lower apposition surface;
   an elongate keel member protruding inferiorly from the apposition surface;
   one or more sharpened pegs protruding inferiorly from the apposition surface;
   one or more elongate protuberating anchors protruding inferiorly from the apposition surface, each protuberating anchor defining a hollow interior through-passage for receiving, mating with, and forming a Morse friction fit with, a tapered screw head received by the through-cavity;
   two or more primary screws, each comprising a tapered head and threaded shaft adapted to form a Morse friction fit; and
   two or more secondary screws, each comprising a threaded cylindrical shaft and sharpened conical tip;
   wherein the secondary screws are placed into the implant prior to surgical impaction of the implant and replaced with the primary screws after surgical impaction of the implant, the primary screws forming a Morse taper with the protuberating anchor adapted to seal the through-passage to prevent osteolysis.

10. The prosthetic implant of claim 9, wherein the hollow interior through-passage consists of an upper section tapered to form a Morse taper with one of the primary screws.

11. The prosthetic implant of claim 9, wherein the hollow interior through-passage consists of a lower section threaded to mate with a secondary screw.

12. The prosthetic implant of claim 9, wherein each conical anchor comprises a frustoconical tip.

13. The prosthetic implant of claim 9, wherein each peg comprises a frustoconical tip.

14. The prosthetic implant of claim 9, wherein the keel is X-shaped through a cross-section.

* * * * *